US009788958B2

United States Patent
Melamed et al.

(10) Patent No.: US 9,788,958 B2
(45) Date of Patent: Oct. 17, 2017

(54) DEVICE AND METHOD FOR HALLUX VALGUS REPAIR BY INTERMEDULLARY SPRING CLIP

(71) Applicants: Eyal Aharon Melamed, Tivon (IL); Matan Lev-Ari Melamed, Tivon (IL)

(72) Inventors: Eyal Aharon Melamed, Tivon (IL); Matan Lev-Ari Melamed, Tivon (IL)

(73) Assignee: Bonfix Ltd., Jerusalem (IL)

( * ) Notice: Subject to any disclaimer, the term of this patent is extended or adjusted under 35 U.S.C. 154(b) by 0 days.

(21) Appl. No.: 14/397,966

(22) PCT Filed: Apr. 29, 2013

(86) PCT No.: PCT/IL2013/050362
§ 371 (c)(1),
(2) Date: Oct. 30, 2014

(87) PCT Pub. No.: WO2013/164819
PCT Pub. Date: Nov. 7, 2013

(65) Prior Publication Data
US 2015/0112446 A1  Apr. 23, 2015

Related U.S. Application Data

(60) Provisional application No. 61/640,077, filed on Apr. 30, 2012.

(51) Int. Cl.
*A61F 2/42* (2006.01)
*A61B 17/56* (2006.01)
(Continued)

(52) U.S. Cl.
CPC ............ *A61F 2/4225* (2013.01); *A61B 17/56* (2013.01); *A61B 17/7266* (2013.01);
(Continued)

(58) Field of Classification Search
CPC ............ A61B 17/7266; A61B 17/7291; A61B 2017/565; A61F 2/4225; A61F 2002/4238
See application file for complete search history.

(56) References Cited

U.S. PATENT DOCUMENTS 4,204,531 A   5/1980  Aginsky
6,127,597 A  10/2000  Beyar et al.
(Continued)

OTHER PUBLICATIONS

Arnold, et al., Biomechanical In Vitro—Stability Testing on Human Specimens of a Locking Plate System Against Conventional Screw Fixation of a Proximal First Metatarsal Lateral Displacement Osteotomy, The Open Orthopaedics Journal, Mar. 8, 2012, pp. 133-139, vol. 6, Bentham Science Publishers, Bethesda, MD.
(Continued)

*Primary Examiner* — Christopher D Prone
*Assistant Examiner* — Suba Ganesan
(74) *Attorney, Agent, or Firm* — Pearl Cohen Zedek Latzer Baratz LLP; Mark S. Cohen

(57) ABSTRACT

A device for repairing Hallux Valgus (HV) is disclosed comprising a first arm adapted to be affixed inside the canal of the first metatarsus (1MT) of a human foot, a second arm adapted to be affixed inside the canal of the second metatarsus (2MT) of a human foot and a spring mechanism connected between the first arm and the second arm, active to push the 1MT closer to the 2MT. The device may comprise fixating means adapted to fixate said first arm inside said MT and said second arm inside said 2MT and the spring mechanism is removable from the first and the second arms.

5 Claims, 16 Drawing Sheets

(51) Int. Cl.
*A61B 17/72* (2006.01)
*A61B 17/80* (2006.01)
*A61B 17/82* (2006.01)

(52) U.S. Cl.
CPC ...... *A61B 17/7291* (2013.01); *A61B 17/8061* (2013.01); *A61B 17/82* (2013.01); *A61B 2017/565* (2013.01); *A61F 2002/4238* (2013.01)

(56) References Cited

U.S. PATENT DOCUMENTS

| | | | |
|---|---|---|---|
| 2009/0036893 A1 | 2/2009 | Kartalian et al. | |
| 2010/0082068 A1* | 4/2010 | Graham | 606/280 |
| 2010/0211071 A1* | 8/2010 | Lettmann et al. | 606/60 |
| 2012/0101502 A1* | 4/2012 | Kartalian | A61B 17/68 606/74 |

OTHER PUBLICATIONS

United States Patent and Trademark Office, "International Search Report and Written Opinion in International Application No. PCT/IL2013/050362", Date: Sep. 13, 2013, USA.

\* cited by examiner

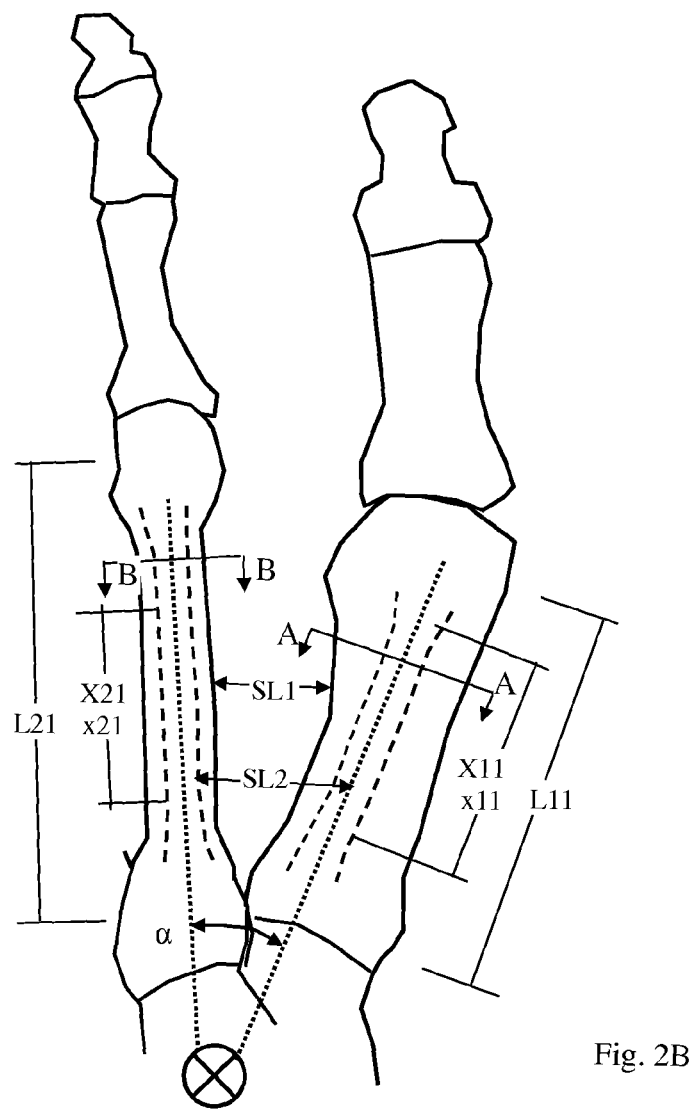
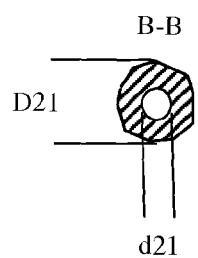
Fig. 2D
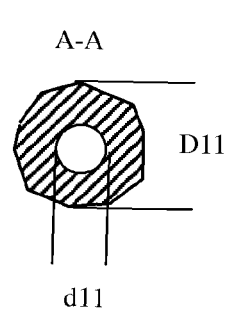
Fig. 2C
Fig. 2B

| Symbol | Description | Range |
|---|---|---|
| L11 | Useful length of canal 1MT | ~40 mm |
| L21 | Useful length of canal 2MT | ~48 mm |
| D11 | Outer diameter of 1MT | ~12 mm |
| D21 | Outer diameter of 2MT | ~6 mm |
| d11 | Inner diameter of canal of 1MT | 10-12 mm |
| d21 | Inner diameter of canal of 2MT | 3-4 mm |
| X11 | Maximal length of intramedullary arm 1MT | 35 mm |
| X21 | Maximal length of intramedullary arm 2MT | 38 mm |
| x11 | Minimal length of intermedullary arm that may provide proper support to spring-1MT | 25 mm (assumption) |
| x21 | Minimal length of intermedullary arm that may provide proper support to spring-2MT | 25 mm (assumption) |
| SL1 | Optional range of free space for installation of spring | From ~15mm To ~10 mm (pending on severity) |
| SL2 | Distance between gripping points | 10-12 |
| α | Range of angle between 1MT and 2MT | |

Fig. 2E

INTRAMEDULLAR
CANAL

DEVICE AND METHOD FOR HALLUX VALGUS REPAIR BY INTERMEDULLARY SPRING CLIP

BACKGROUND OF THE INVENTION

Hallux valgus (HV) is a common foot deformity in which the big toe (the Hallux) deviates into the lateral or outer side of the foot (valgus deviation). This is accompanied by deviation of the first metatarsus (MT, 1MT) inward (varus). The two processes e.g. metatarsus varus and hallux valgus are linked Part (and at times all) of the repair means known in the art is aimed to reduce the varus deviation of the 1MT. The varus deviation of the 1MT increases the angle between that bone and the $2^{nd}$ MT (2MT) creating a wide intermetatarsal angle (IMA). HV degree is defined as the angle between the longitudinal axis of 1MT and the axis of the proximal phalanx of the Hallux, and is expressed as HV angle (HVA). The two main parameters which define the HV degree are the HVA and IMA.

Accordingly, in surgery the goals are to reduce both angles. The basic or common prior art surgery often aims to correct the IMA by sawing the 1MT and shifting its distal part toward the $2^{nd}$ MT. Attempts to correct the IMA without sawing the 1MT, as known in the art, incorporate usually a suture or a cable that is passed between 1MT and 2MT. the most common is the Mini Tightrope© endo-button device. These modes entail inherent problems including reported up to 30% of fractures of the $2^{nd}$ MT.

SUMMARY OF THE INVENTION

A device for repairing Hallux Valgus (HV) according to embodiments of the present invention is disclosed comprising a first arm adapted to be affixed inside the canal of the first metatarsus (1 MT) of a human foot, a second arm adapted to be affixed inside the canal of the second metatarsus (2MT) of a human foot and a spring mechanism connected between said first arm and said second arm, active to push said 1MT closer to said 2MT. According to some embodiments the device may further comprise fixating means adapted to fixate said first arm inside said 1MT and said second arm inside said 2MT and the spring mechanism is removable from the first and the second arms.

According to yet other embodiments the spring mechanism may be adapted to be connected to the first arm and the second arm after the first and the second arms are installed and affixed inside said 1MT and 2MT respectively.

According to some embodiments the spring mechanism may be adapted to provide a first pulling force between the first and the second arms in a first plane being the plane common to said 1MT and 2MT and a second pulling force between the 1MT and 2MT in a plane perpendicular to said first plane.

According to some embodiments at least one of the first and the second arms is affixed to its respective MT by fixing means wherein the fixing means is at least one from the list consisting: friction unit, fixating screw and clamp.

According to some embodiments the first arm comprising a first portion being formed as a longitudinal tubular structure slightly banana-like bent and a second portion close to the proximal end of said first portion angled with respect to said first portion and provided with a gripping point close to its proximal end adapted to connect to said spring mechanism.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 2B is a schematic illustration of 1MT and 2MT of a human foot with indications of certain physical dimensions;

FIG. 2C is a schematic illustration of a cross section of 1MT of FIG. 2B;

FIG. 2D is a schematic illustration of a cross section of 2MT of FIG. 2B;

FIG. 2E is a table presenting typical values of physical dimensions presented in FIGS. 2B, 2C and 2D;

It will be appreciated that for simplicity and clarity of illustration, elements shown in the figures have not necessarily been drawn to scale. For example, the dimensions of some of the elements may be exaggerated relative to other elements for clarity. Further, where considered appropriate,

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Figure 1A:
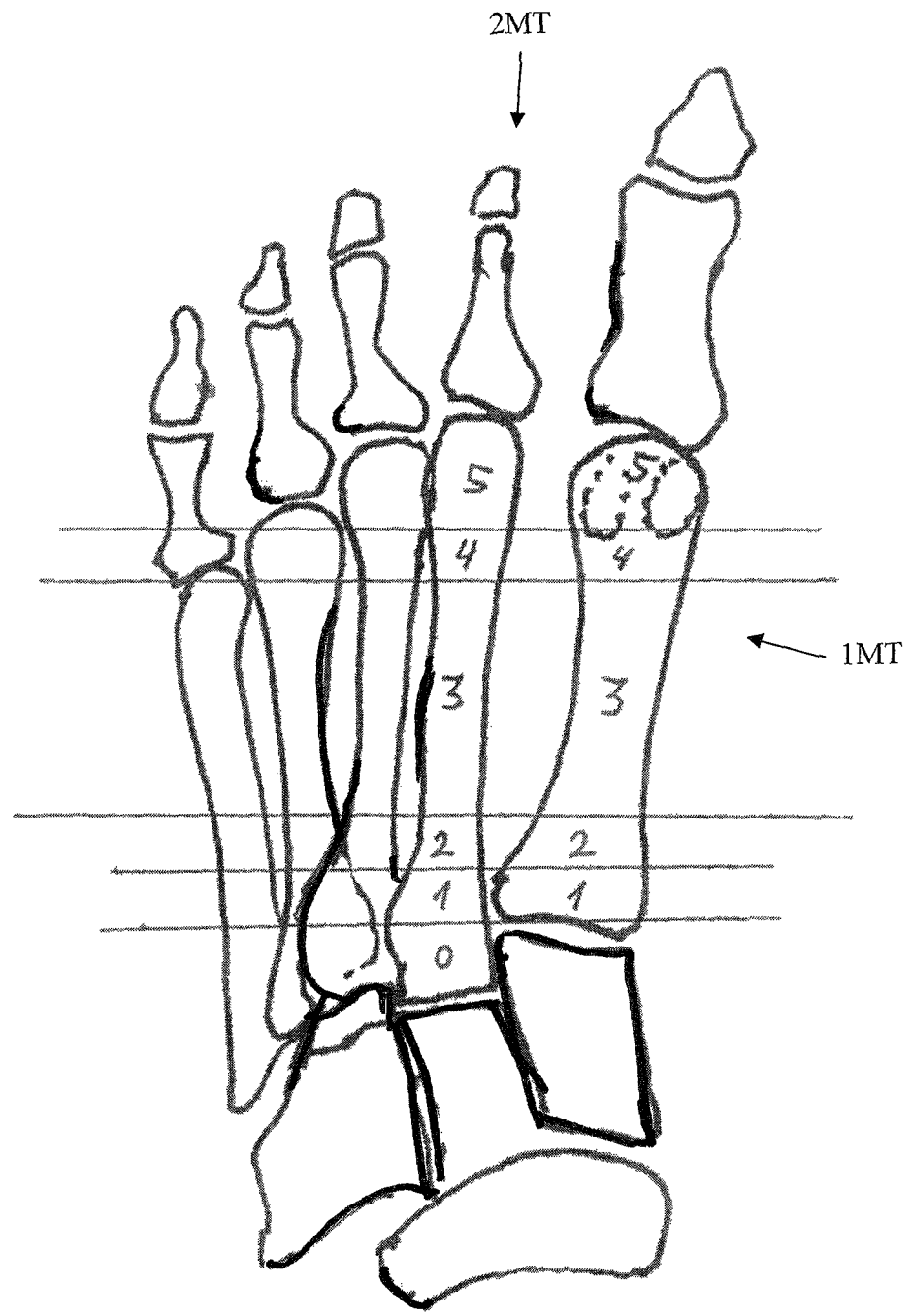
FIG. 1A is schematic illustration of a human foot, presenting schematic partition of the foot's bones to 5 longitudinal sections.

Reference is made now to FIG. 1A, which is schematic illustration of a human foot, presenting schematic partition of the foot's metatarsal (forefoot) bones to 6 longitudinal sections.

Descriptive Anatomy, 1-2 Metatarsal Zones

In order to understand and direct the introduction and placement of a device according to embodiments of the present invention into, or onto the 1MT and 2MT, six (6) zones in the 1MT and 2MT have been defined as seen in FIG. 1. These zones relate to the shape of the 1MT as seen in the radiologic AP view as well as to the distance between the adjacent cortices of the $1^{st}$ and $2^{nd}$ MT's.

Zone 0 is the base of 2MT, which is located between the adjacent cuneiforms. There is no contact between 1MT and 2MT at that region. However, a strong plantar ligament, the Lisfranc ligament that originates from the medial cuneiform inserts on the plantar aspect of the base of 2MT. This ligament may keep the first ray and $2^{nd}$ ray close together, so it can be seen as a hinge, on which the 1MT deviates from the 2MT. There are question about the existence, measurements and importance of the hypermobile $1^{st}$ ray. Often, in cases of hypermobile $1^{st}$ ray the planned surgery is to fuse the joint between the medial cuneiform and the 1MT (Lapidus procedure). Some surgeons fuse at the same time the base of the $2^{nd}$ MT as well, to create a stiff configuration between the $1^{t}$ and $2^{nd}$ MT's.

Hypermobility of the $1^{st}$ ray is checked mainly as translation in the dorsal-plantar plane, but at times, medial displacement is observed at the base of the 1MT. It is therefore logical to view the Lisfranc ligament as the safe (and constant) axis of the motion between 1-2MT.

Zone 1 is at the very base of 1MT. At that point usually t1MT is parallel to 2MT and forms a joint with it. The distance between the two is minimal (practically there is no distance between them at the proximal part). The distal part of Zone 1 is just when the lateral cortex of the MT starts to form a bent, which is the transition point from $1^{st}$ to $2^{nd}$ zone. At this point there is slight widening between the two MT's, which is responsible for the slope of region 1.

Zone 2 is the area of slope where the 1MT deviates further away from 2MT. the measured slope at this region is roughly about 6.0 mm/1.0 cm. this slope encompass also the slight deviation and narrowing of the 2MT at this zone. The length of zone 2 is 8.5-10.5 mm.

Zone 3 is the zone where the two MT's are separated, and in this region in the normal patient without Hallux Valgus the distance between the MT's is almost constant (there is small curve in this region but this is insignificant. The length of zone 3 is 24-30 mm. The importance of these regions is that in some of the embodiments they direct the shape and the entrance location of the device or the more convenient location to apply the arms of the device on each of the metatarsals. It is convenient and spacious in this zone to contain the spring mechanism or the bulk of the mechanism.

Zone 4 is the neck region, in this zone the MT's shaft start their expansion toward the head. The bone is becoming wider. The bone changes from diaphyseal to metaphyseal and the relatively loose canal gives way to spongeiotic bone. The relevance of this zone is that it may be difficult to a blunt tip to penetrate into it from the intramedullary canal without resistance. However, at the same time this implies that the tip of an intramedullary device may get good or reasonable purchase in that region.

Zone 5 is the head Zone. The distance in the AP view between the borders of the MT may narrow to 4.0 mm (range ~3.0-6.0 mm in the non HV foot). Table 1 below presents typical longitudinal and latitudinal dimensions of a human foot

TABLE 1

| Dimensions of Metatarsal Zones (FIG. 1A) | | | | | |
|---|---|---|---|---|---|
| Zone | Description | Length | Width Proximal | Width Distal | Delta Width | Slope mm/cm |
| 0 | base of 2nd | 9.5 | 1.0 | 1.36 | 0.4 | 0.4 |
| 1 | base of 1st | 7.5 | 1.4 | 3 | 1.6 | 2.2 |
| 2 | slope zone | 10.2 | 3.0 | 9.15 | 6.2 | 6.0 |
| 3 | static zone | 28.8 | 9.2 | 12 | 2.9 | 1.0 |
| 4 | neck zone | 9.5 | 12.0 | 9.75 | −2.3 | −2.4 |
| 5 | head zone | 18.4 | 9.8 | 4 | −5.8 | NA |

Measurements were done on an average man without Hallux valgus.
His IMA ~4.5 degrees.

The various zones are presented in FIG. 1A

Sizes and Measurements

The width and length of the metatarsals were studied to get an impression of the physical constrains that apply to a device according to embodiments of the present invention. The average width of the 2MT is 7.6 mm in women (N=12) and 8.4 mm in men (N=6), as presented in Table 1:

TABLE 2

| $2^{nd}$ MT Midshaft width | $1^{st}$ MT Midshaft width | | |
|---|---|---|---|
| 9.5 mm | 14.9 mm | N = 6 | Average size for men |
| 7.6 mm | 12.6 mm | N = 12 | Average size for Women |

The width of the longitudinal canal of the 2MT was measured (the measure between the inner sides of the cortices) and was found to be roughly 40-50% of the outer diameter of the shaft. This means that the outer diameter of an implant in the 2MT needs to be in the order of 2.5 to 4.0 mm. In the 1MT the width may be much larger, in the order of 11.5-12.5 mm in diameter. The inner diameter, which reflects the canal diameter, is much larger in the 1MT compared to the 2MT, and is roughly ⅔ of the outer diameter of the 1 MT. This means that the canal diameter in the narrowest spot is about 8.0 mm (range 7.0-9.0 mm).

Dorso-Plantar Morphology and Declination Angle

Looking at the sagittal plane or a lateral view weight bearing X ray reveals that there is declination angle to the metatarsals. Traditionally this is considered as 20° down slope for the 1st MT, 15° to 2MT, and 12°, 10° and 8° to the 3rd, 4th and 5th MT. The implant planning should relate to these values but more so it shall take care of the relative motion between 1MT and 2MT.

Another morphological parameter that needs to be understood is the slope of the plantar cortex of the metatarsals 1-4.

They all are much wider at the base in the dorsal-plantar aspect. The upper part is more or less flat. The slope of the base occupies about one third of the length of 1MT and roughly one quarter of the length of 2MT-4MT. The relationship between the slope and the Zones of the 1MT, as described for the purpose of inserting the device can be seen.

Figure 1B:
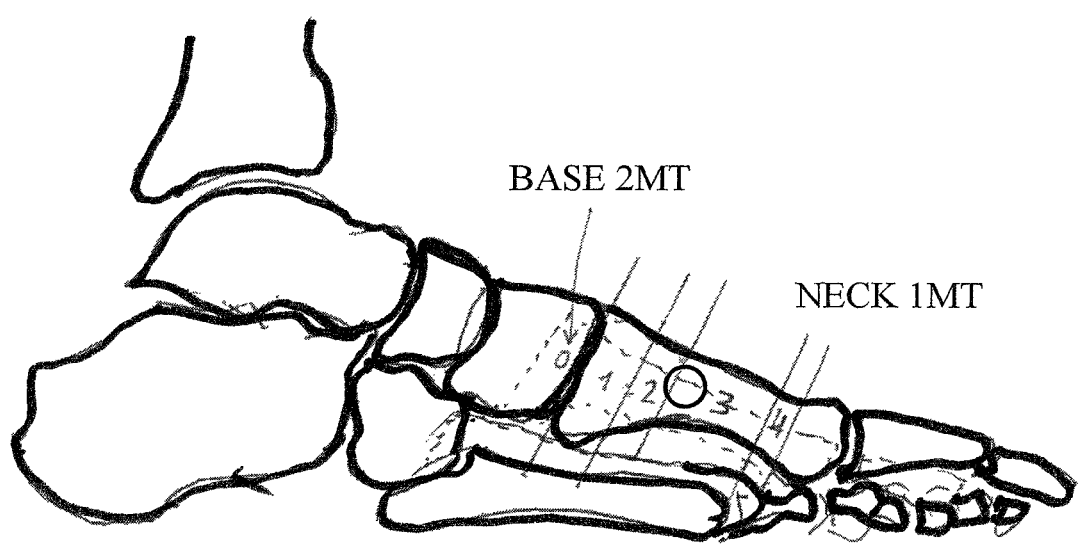
FIG. 1B is a lateral weight bearing schematic illustration demonstrating the general configuration of the 1MT in the foot.

1MT and 2MT Zones description in LAT view of the foot: Reference is made to FIG. 1B which is a schematic illustration lateral weight bearing view of the foot demonstrating the general configuration of the 1MT. FIG. 1B also depicts the zones on the lateral view. The desired entrance region of an internally installed arm is marked by thick circle.

Metatarsal Cortex Thickness

It is of noteworthy for further understanding the rational of some of the embodiments of this invention (e.g. the intramedullary arms construct) to clarify the thickness of the metatarsal cortices. The lateral cortex of 1MT and the medial cortex of 2MT are significantly (roughly about 30% more) thicker than the adjacent cortex of the same metatarsal. This thickness implies increased load and increased strength; hence the metatarsals are expected to be more resistant to forces acting on these cortices than the medial cortex of 1MT and the lateral cortex of 2MT.

Embodiments of a device and method of treatment according to the present invention may comprise of a device with two arms that are connected to each other in a springiness manner so that a springy force acts to pull the two arms close to each other. The arms produce, each, a basis for a gripping point which is firmly attached to its respective MT. The gripping points may be connected by a spring-like element in order to enable activation of the springy force onto the MTs.

Figure 2A:
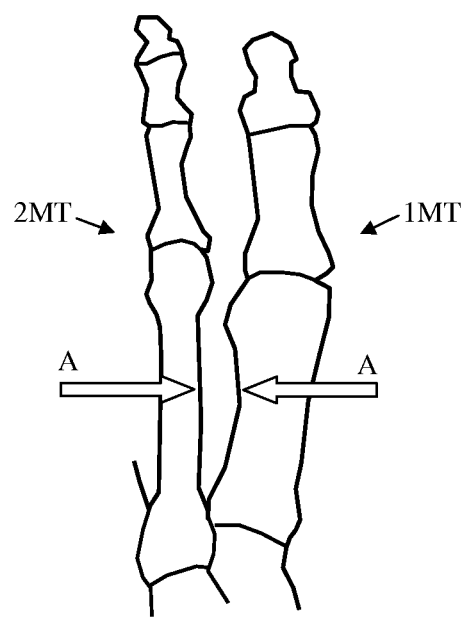
FIG. 2A schematically represents the forces and free movements required from a device according to the present invention, which act on the 1MT and the 2MT.

According to some embodiments one of the arms may be inserted into the medullary canal of 1MT and the other into the medullary canal of the 2MT, as is described in details herein below. Reference is made now to FIG. 2A, which schematically represents the forces and free movements required from a device according to the present invention, which act on the 1MT and the 2MT according to embodiments of the present invention. The design of the arms and the spring-like mechanism aims to ensure the existence of springy force acting between the 1MT and the 2MT in the plane of the paper as depicted by arrows AA and allowing the needed relative freedom of movement between the 1MT and the 2MT in a plane perpendicular to the plane of the drawing of FIG. 2A.

In the intramedullary embodiment the forces between 1MT and 2MT are acting mainly on the lateral cortex of 1MT and the medial cortex of 2MT.

Reference is made now to FIG. 2B, which is schematic illustration of 1 MT and 2MT of a human foot with indications of certain physical dimensions. The dimensions which are indicated are those that may be required for the proper design of physical dimensions of a device for repairing Hallux valgus, according to embodiments of the present invention. The dimensions are the length of the medullary canal of 1MT useful for the device according to the invention (L11); the length of the medullary canal of 2MT useful for the device according to the invention; the maximal length of an arm of a device according to embodiments of the present invention when installed in the medullary canal of 1MT (X11); the maximal length of an arm of a device according to embodiments of the present invention when installed in the medullary canal of 2MT (X12); the minimal length of an arm of a device according to embodiments of the present invention when installed in the medullary canal of 1MT, that may provide desired support (x11); the minimal length of an arm of a device according to embodiments of the present invention when installed in the medullary canal of 2MT, that may provide desired support (x21); the width of the space between 1MT and 2MT in the $3^{rd}$ section, which is available for positioning a spring mechanism according to embodiments of the present invention (SL1); the distance between gripping points of the first and second arms of a repair device according to embodiments of the present invention (SL2); and the angle between an imaginary line running through the medullary canal of 1MT and that of 2MT (a).

Reference is made now to FIGS. 2C and 2D, which are schematic illustrations of cross section of 1MT and 2MT of FIG. 2B respectively. Cross sections of 1MT (FIG. 2C) and of 2MT (FIG. 2D) are made at the cross section lines A-A and B-B, respectively, in the 1MT and 2MT in the $3^{rd}$ section. The dimensions are the outer diameter of 1 MT at a location along L11 (D11); the outer diameter of 2MT at a location along L21 (D21); the inner diameter of the medullary canal of 1MT (d11); the inner diameter of the medullary canal of 2MT (d21).

Reference is made now to FIG. 2E, which is a table presenting typical values of physical dimensions presented in FIGS. 2B, 2C and 2D. It will be appreciated by those skilled in the art that the dimensions are typical and that each personal human foot may have corresponding dimensions that may deviate from the values in the table by a certain extent. Accordingly a repair device according to embodiments of the present invention shall be personally adapted to a specific person by, inter alia, by selecting personal values for the respective physical dimensions.

A basic design of a device according to embodiments of the present invention may comprise two arms connected to each other or to a spring mechanism at one of their ends. In the basic embodiment the arms are built to introduce into the medullary canal of 1MT and 2MT and hold there snugly. A springy force acting to bring the arms closer to each other when placed in the treated foot is achieved by the shape of the arms, the connection between them to a spring mechanism and a designed construction of the spring mechanism. According to some embodiments of the present invention the spring-generated force may be in the range of 20-40N.

Figures 2F, 2G:
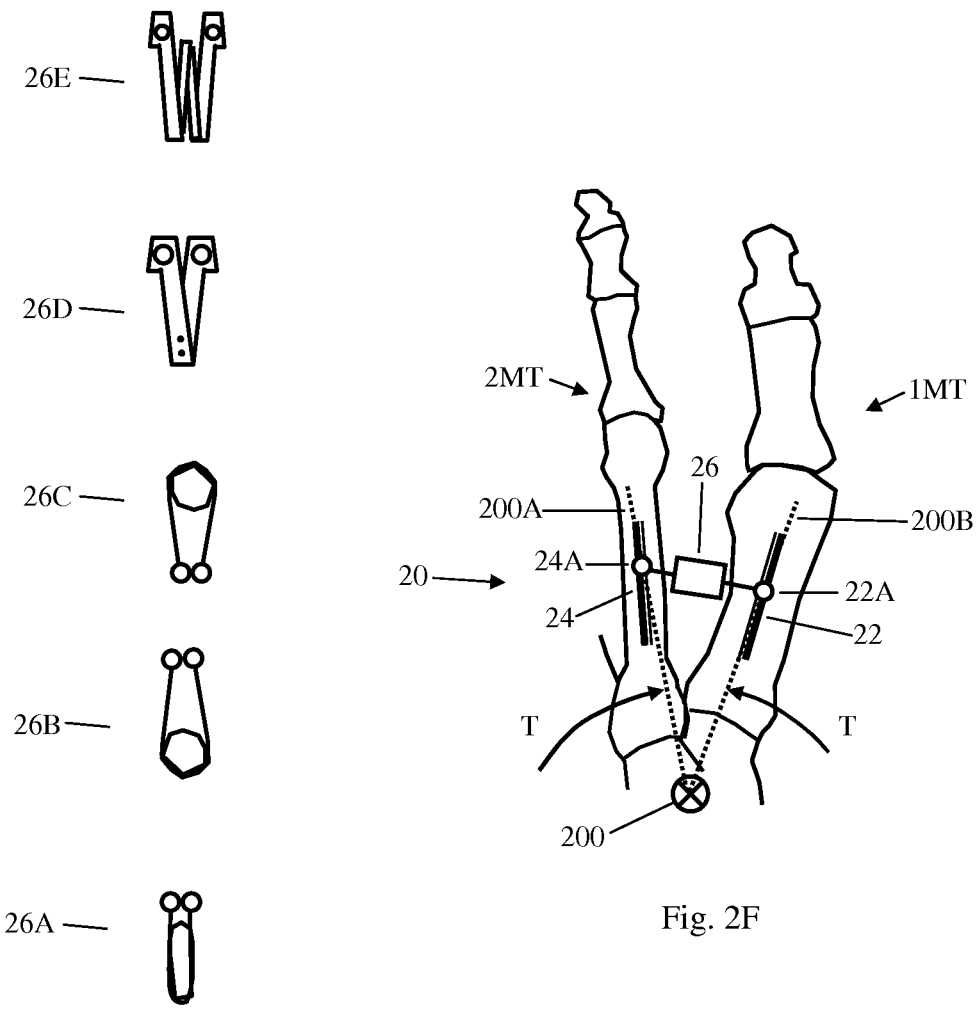
FIG. 2F schematically presents an HV repair device according to embodiments of the present invention.
FIG. 2G depicts three exemplary configurations of a spring-like mechanism, according to embodiments of the present invention.

The relatively big difference between the canal size in 1 MT compared with that of the 2MT may have an impact on the design, the size and shape of the arms of a device of the relevant MTs, according to embodiments of the present invention. Reference is made now to FIG. 2F, which schematically presents HV repair device 20 according to embodiments of the present invention. HV repair device 20 may comprise a first arm 22 to be affixed to one of 1MT shanks, a second arm 24 to be affixed to one of 2MT shanks and spring-like mechanism 26 connected to first arm 22 and second arm 24 so as to apply springy force to rotate about pivotal point 200 bring first arm 22 and second arm 24 close to each other. It will be apparent to those skilled in the art that the exact form and location of each of the first and the second arms with respect to 1MT and 2MT, respectively, and the exact way of affixing each of the arms to its respective MT, may vary according to the specific design of HV repair device 20. Similarly, the exact form, springy features and location of spring-like mechanism 26 with respect to first arm 22 and second arm 24 may vary. The schematic action of HV repair device 20 may be better understood with the assistance of imaginary pivotal point 200 located proximal to the base of 1MT and 2MT and imaginary radials 200A and 200B beginning at pivotal point 200 and extending through the points where spring-like mechanism 26 is connected to arms 22 and 24, respectively. In some embodiments of the present invention where the spring-like mechanism acts directly on the ends of arms 22, 24 proximal to pivotal point 200, as will be explained below the spring-like force exerts torque to the arms as depicted by arrows T. The effect of spring-like mechanism 26 on 1MT and 2MT may be explained, with very good approximation, as a movement about pivotal point 200 so that the angle α between radials 200A and 200B get smaller as the repair progresses. Concurrently, the way arms 22 and 24 are connected to each other allow enough freedom of movement of 1MT and 2MT with respect to each other in a direction perpendicular to the direction of the movement getting 1MT and 2MT close to each other.

Reference is made now to FIG. 2G, which depicts three exemplary configurations of a spring-like mechanism 26A, 26B and 26C, according to embodiments of the present invention. All three examples may provide a pull-together torque force onto arms 22 and 24.

There are few possible configurations of the arms according to embodiments of the present invention. In case of arms that are affixed to the treated MT by insertion into the medullary canal, the arms should be somewhat tapered and curved at their tip to allow gliding penetration into the medullary canal of the respective treated fingers, e.g. 1MT and 2MT, through a drill hole. The design of the arms is influenced by the shape and width of the medullary canal. In the 1MT the canal is wide, in the order of 9-12 mm. the arm that is introduced through a smaller hole needs to have significant expandable capabilities in order to achieve snug fit in the MTs.

When a HV repair device according to embodiments of the present invention includes intramedullary arms for introduction purposes the device should preferably be composed of three separable basic elements-two arms and a spring mechanism element that may be connected, each in its preferred time, before or during surgery, as may be convenient thus leaving maximal comfort in introduction and assembling of the device. According to some embodiments the HV repair device may be produced of a single unit comprising two arms and a spring mechanism or of two elements one comprising an arm and a spring mechanism and the other comprising an arm. These basic parts may be a first arm that may be connected to 1MT, a second arm that is connected to 2MT and a spring or spring like mechanism attaching said first and said second arms. The arms or spring mechanism are manufactured to exert a defined width and elastic force between them, with direction to pull the arms towards each other. The device may be inserted into the relevant MT's through a small cut on the dorsum of the foot close to the bases of the two MT's or through a similar but extensile approach. In yet another embodiment the penetration point into the MT medullary canal can be at a more distal point with the arm of each said MT holding both distally from and proximally to the entrance point.

Figure 3:
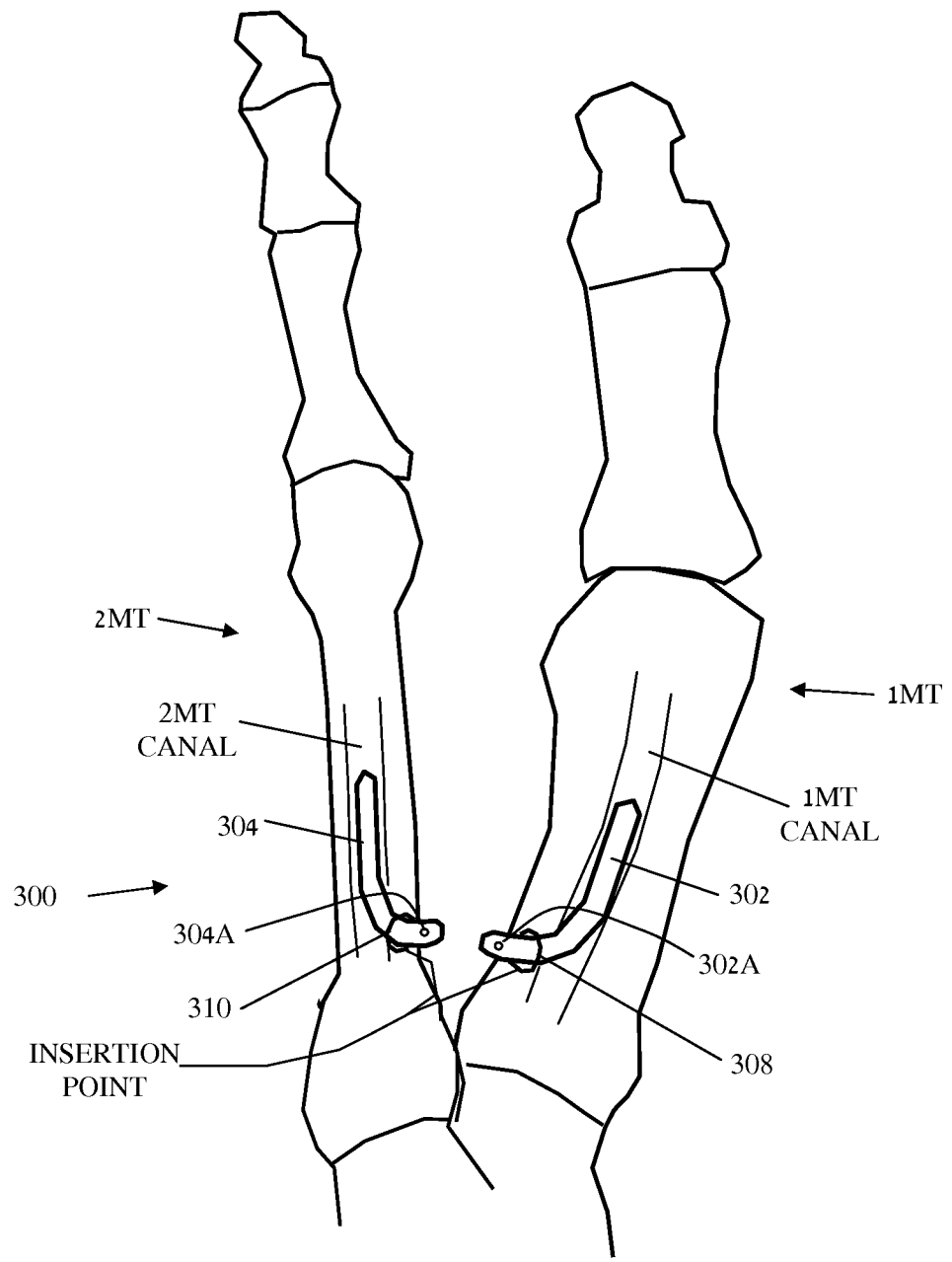
FIG. 3 schematically depicts location of arms in 1MT and 2MT of a repair device according to embodiments of the present invention.

Reference is made now to FIG. 3, which schematically depicts location of arms in 1MT and 2MT of repair device 300 according to embodiments of the present invention. Repair device 300 may comprise 1MT arm 302 and 2MT arm 304, shown in their final insertion position in the respective MTs. The spring-like mechanism is not shown for the sake of clarity in order to not obscure the drawing. Each of arms 302, 304 may be formed and may have the dimensions according to the specific MT as well as other considerations, as will be discussed in details herein below. Each of arms 302, 304 may have a gripping point 302A, 304A, respectively, formed at its proximal end that protrudes out of the bone, and if necessary out of the tissue surrounding the bone. Gripping points 302A, 304A are made to enable attaching the spring-like mechanism. In order to enable insertion of the arms into the MT canal a small hole may be drilled through the MT cortex, for example at the location marked in the drawing INSERTION POINT, however other locations may be selected, as may be required. Insertion of the arms may pose some difficulties depending on the size of the canal, the required tolerance of the arm in the canal, etc. The length, shape and diameter of the arms may be calculated to meet these constrains. An arm that was inserted into the canal may be subject to sliding out forces as well as torsional or rotational forces. Accordingly fixating designs comprised on snug fit or complementary screw(s) and/or pin(s) are required. Throughout the description of embodiments of the present invention the tem "fixating means" refers to one or more of means for securing an element to a bone or a portion of a bone including anti-sliding means, anti rotational means and anti-toggling means, such as screws, friction, clamps, etc.

Figure 4:
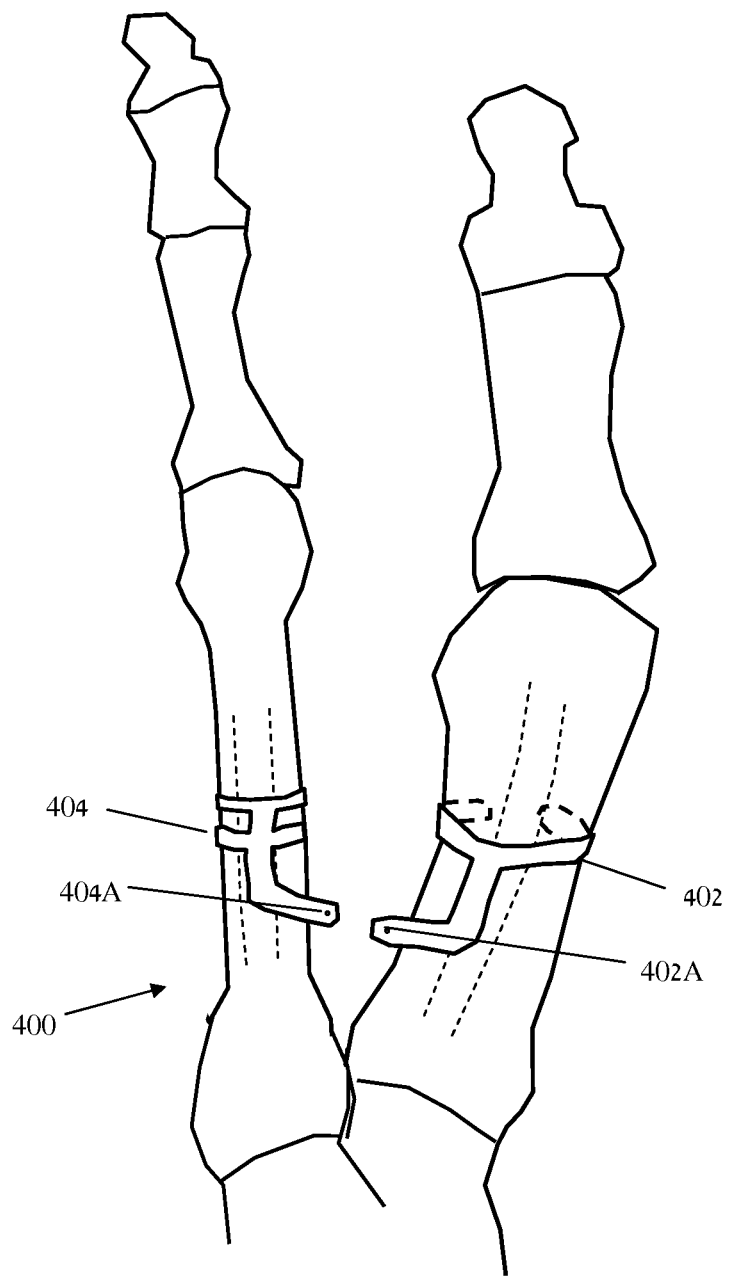
FIG. 4 schematically depicts location of arms in 1MT and 2MT of a repair device according to yet other embodiments of the present invention.

Reference is made now to FIG. 4, which schematically depicts location of arms in 1MT and 2MT of repair device 400 according to yet other embodiments of the present invention. Repair device 400 may comprise 1MT arm 402 and 2MT arm 404, built as clamps which embrace the MTs on their outside circumference as depicted in the drawing or may be attached to the outer face of the MT (not shown), shown in their final position on the respective MTs. The spring-like mechanism is not shown for the sake of clarity in order to not obscure the drawing. Each of arms 402, 404 may be formed and may have the dimensions according to the specific MT as well as other considerations, as will be discussed in details herein below. Each of arms 402, 404 may have a gripping point 402A, 404A, respectively, formed at its proximal end that protrudes away from the face of the bone, and if necessary out of the tissue surrounding the bone. Gripping points 402A, 404A are made to enable attaching the spring-like mechanism. An arm that was placed and clamped on the MT may be subject to sliding forces tending to move it from its location. Accordingly anti-sliding fixating designs are required. In the simple form this may be achieved with a screw or screws inserted through holes in the clamp. Preferably these will be locking screws. Tight fit of the clamp may serve as an anti-rotational motion. Sharp pin or fins or hooks may achieve similar goals.

Figure 5:
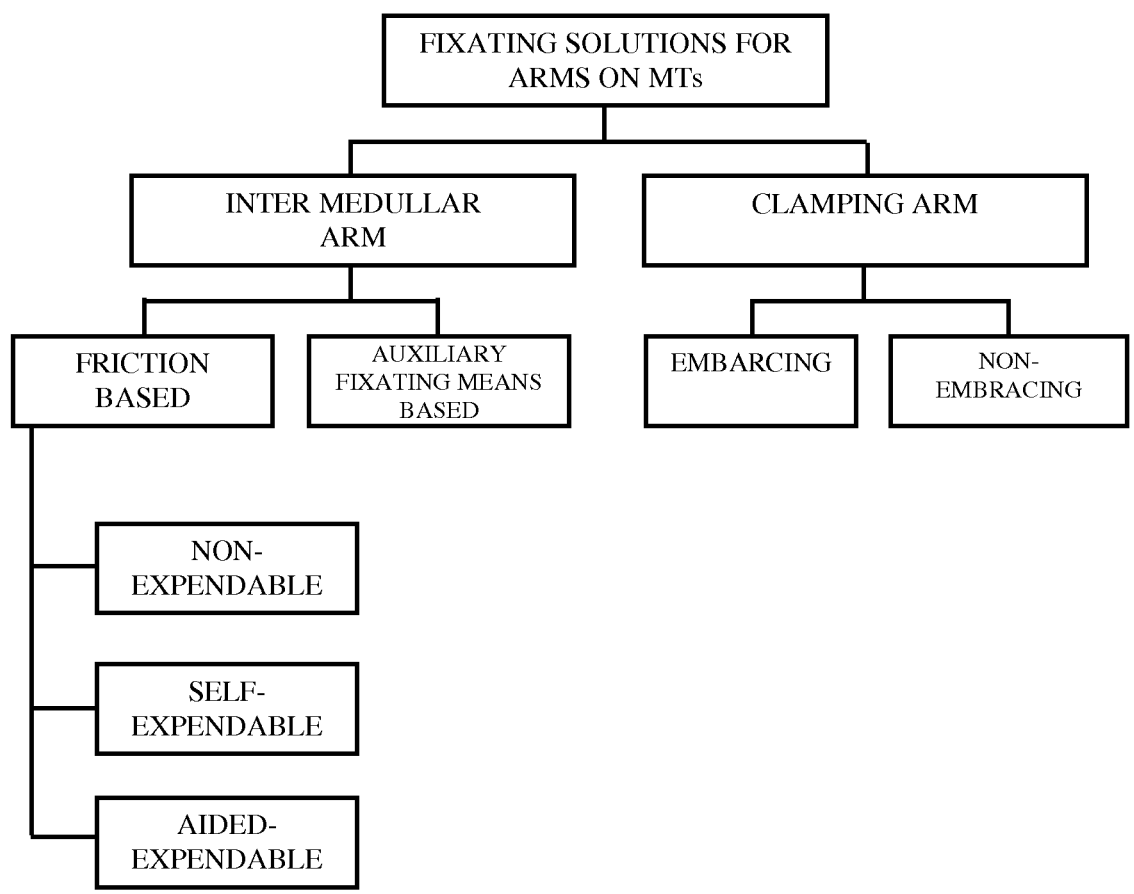
FIG. 5 is a block diagram presenting the various means and methods for affixing arms of a HV repair device to their location on the respective MT, according to embodiments of the present invention.

Reference is made now to FIG. 5, which is a block diagram presenting the various means and method for affixing arms of a HV repair device to their location on the respective MT, according to embodiments of the present invention. As seen, fixating means according to embodiments of the present invention may be divided into two main groups. First group includes means for internal fixtures (e.g. internal to the MT), typically fixating intramedullary arms. A second group includes means for fixtures that are external to the MT, such as fixating clamping arms. The first group, of means for fixating intramedullary arms, may be divided to two groups. First group of fixating means for intramedullary arms is based on friction between the arm and the medullar canal. Second group of fixating means for intramedullary arms is based on auxiliary fixating means. The second group of means for fixating clamping arms or plates, may be divided to two groups. First group of fixating means for fixating clamping arms includes embracing arms. Second group of fixating means for fixating clamping arms includes non-embracing arms.

The first group of fixating means for intramedullary arms which is based on snug fit or high friction between the arm and the medullar canal may be divided to 3 sub groups: non-expandable means, self expandable means and aided expandable means. In many of the embodiments it is possible to coat the implant with hysroxyapatite or any other known material that promotes incorporation between the arm and the MT bone. However, it is preferable to abolish movement at the initial period after the surgery.

U.S. Pat. No. 6,127,597 to Beyar et al. describes various fixating means for fixating bones. U.S. Pat. No. 4,204,531 to Aginsky describes expandable nail for repairing broken bone. However neither Beyar et al. nor Aginsky describe means for affixing an arm of a HV repair device to a bone nor are they meant to intact not broken bone.

Figure 6A:
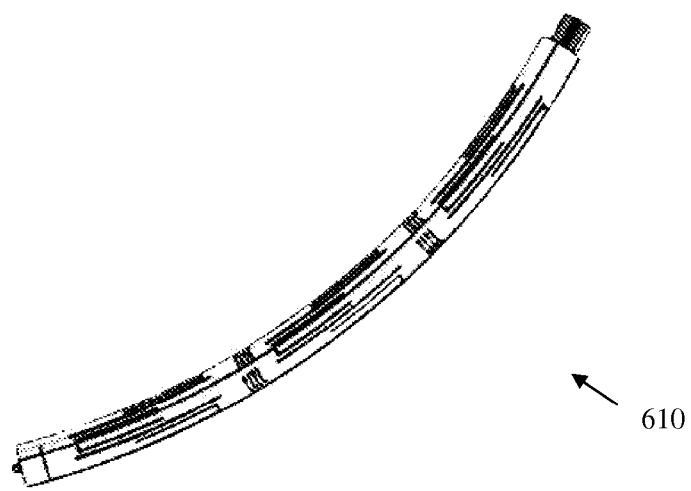
FIG. 6A schematically presents an intramedullary arm, according to embodiments of the present invention.

Reference is made now to FIG. 6A, schematically presenting intramedullary arm 610 which may be associated with the first group of fixating means for intramedullary arms which is based on friction between the arm and in it with the sub group of non-expandable means, according to embodiments of the present invention. Arm 610 may have curved banana shape configuration, which ease the insertion of the arm into the medullary canal of the 1MT or 2MT, while gaining good grip of the inner walls of the canal when placed in the right position. Additionally or alternatively the outer face of arm 610 may be formed with slight delicate wavy configuration (not shown) to enhance the gripping of the arm in the canal. It will be apparent to those skilled in the art that since the sliding-out force acts substantially along the longitudinal axis of 1MT or 2MT, the repair force of the spring-like mechanism (not shown) acts substantially perpendicular to the longitudinal axis of the MT. Accordingly, relatively small anti-sliding force may be required to ensure good grip of the arm. When the size and form of arm 610 does not fully overlaps that of the respective portion of the medullary canal, when arm 610 is placed in its position good grip may be achieved due to the slight differences in form and size, which exerts compression and tight fit between arm 610 and the medullary canal. It would apparent to those skilled in the art that an osseo-integration agent may be used to develop growth of the inner face of the bone into the arm, to provide additional or, by the time, alternative fixating means.

Figure 6B:
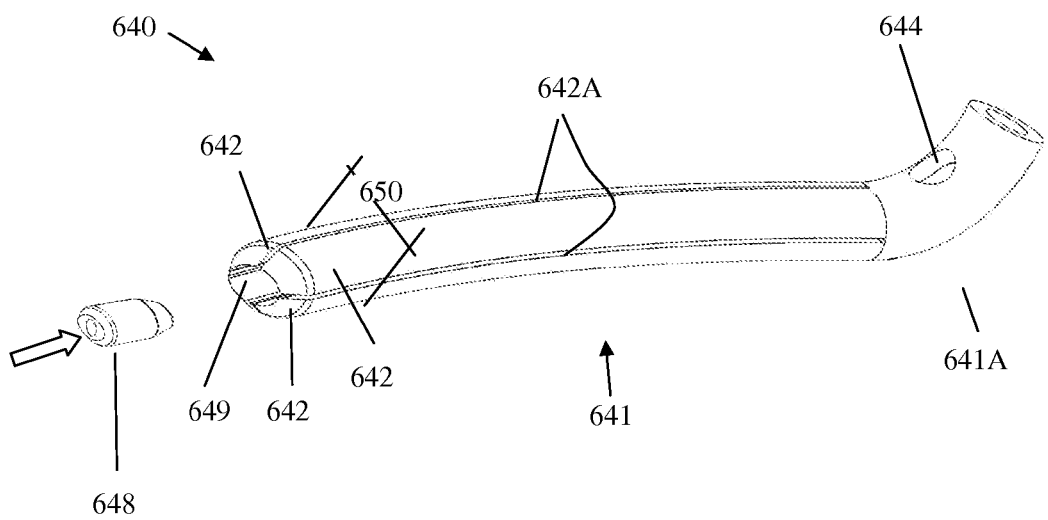
FIG. 6B schematically presents an expandable arm, according to embodiments of the present invention.

Reference is made now to FIG. 6B, which schematically presents expandable arm 640, according to embodiments of the present invention. Arm 640 may be formed of a main longitudinal portion 641 having a longitudinal bore along it and a bent portion 641A at its proximal end (the end that protrudes from the medullar when installed) gripping point 644. Arm 640 may further comprise a widening cone 648. Arm 640 may have, additionally to its basic banana-like form, at least two longitudinal slices, or slats 642 made along at least part of the length of portion 641, separated by longitudinal thin cuts 642A. Slats 642 may be formed so as to have, in their natural position, an outer diameter 650 which is slightly smaller than the inner diameter of the respective medullary canal. Widening cone 648 may be adapted to put apart the distal ends of slats 642 apart when it is pushed into the widening cavity 649. Widening cone 648 may be adapted to be pushed into cavity 649 in one of known methods, such as be pushed when arm 640 is in the end of its insertion movement, or by pulling an activation wire, or similar pulling means, that may run outwardly through the longitudinal cavity in arm 640, and the like. Accordingly, when arm 640 is inserted into the medullary canal and widening cone 648 is pushed, or pulled into widening cavity 649, slices 642 are forced outwardly by the pressure of widening cone 648 and as a result stronger compression and tight fit force is created. Arm 640 may serve as an example to the second group of fixating means for intramedullary arms which is based on aided-expanding devices. It will be appreciated that other forms and designs that may achieve expansion of intramedullary devices such as, among other, folded nails or rods, rods with springy curvature that is inserted straight, either in a sleeve container or by means of temperature-sensitive effect that allows easy insertion. Expansion of the nail may also be achieved by pushing a second said flexible rod that is slightly larger than the inner diameter of the first element (rod).

Figure 6D:
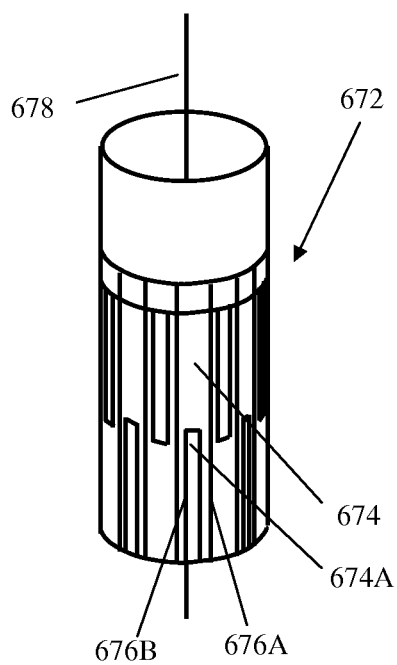
FIGS. 6C and 6D schematically present an intramedullary friction locking device and an expanded view of one of its elements, respectively, according to embodiments of the present invention.
Figure 6C:
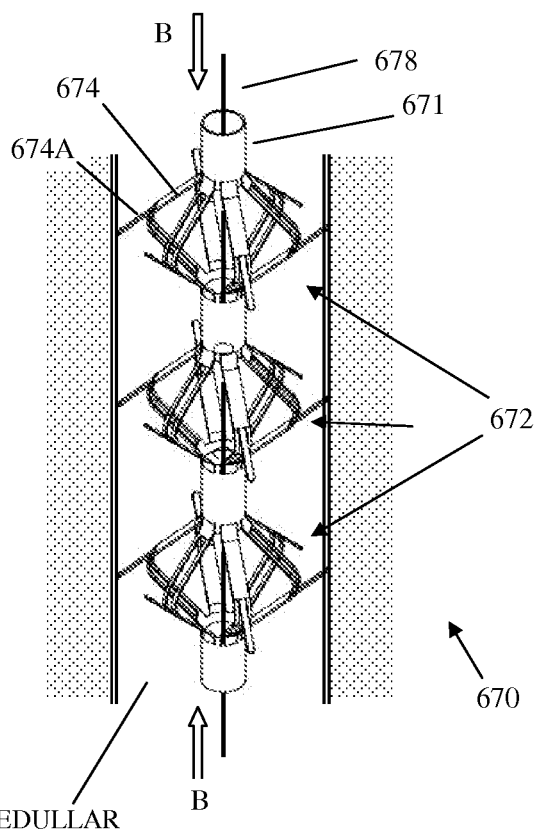

Reference is made now to FIGS. 6C and 6D, which schematically present intramedullary friction locking device 670 and an expanded view of one of its elements, respectively, according to embodiments of the present invention. Locking device 670 may comprise one or more expandable friction locking units 672, formed along a tubular structure 671. An initial position of device 670 is in closed position, as depicted in FIG. 6D. The wall of tubular structure 671 may be made of thin relatively hard but bendable material, such as thin tin. Very narrow longitudinal cuts 676A may be prepared, along most of the length of unit 672, defining plurality of slices 674 around the circumference of unit 672. In each slice 674 a longitudinal U shaped cut 676B may be made, defining a locking anchor 674A. When friction locking device 670 is in its initial position the tubular form is maintained and friction locking device 670 may be inserted into a medullary canal easily. When placed in the right location friction locking units may be expanded for example by pulling activation wire 678 so as to shorten the initial length of friction locking device 670. As a result slices 674 collapse and bend outwardly and locking anchors 674A protrude sharply and lock onto the internal walls of the medullary canal, as seen in FIG. 6AC. It will be appreciated by those skilled in the art that the number of expanding locking units 672, the number of circumferential slices, the selection of the material of the unit, activation mechanism, etc. may be done to meet the specific requirements, such as the required anti-sliding force, the anti-rotational and anti-toggling motion, the dimensions of the medullary canal, etc.

Figure 7A:
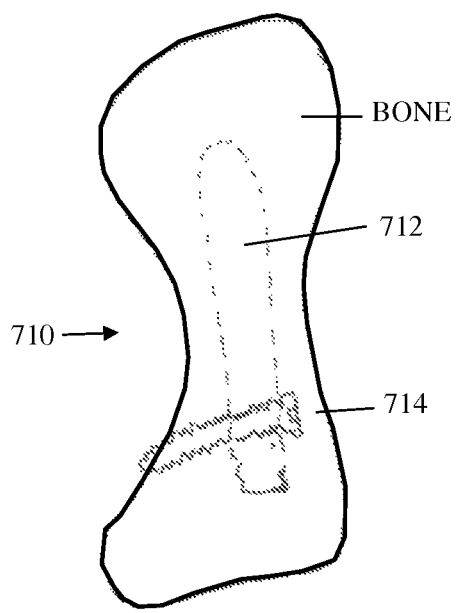
FIGS. 7A to 7E depict schematic illustrations of arrangements for fixating intramedullary arm according to embodiments of the present invention.
Figure 7B:
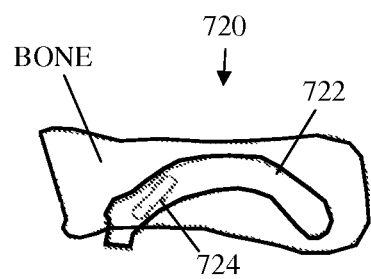
Figure 7C:
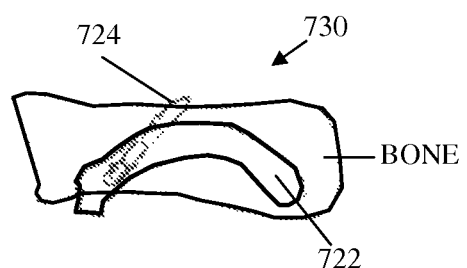
Figure 7D:
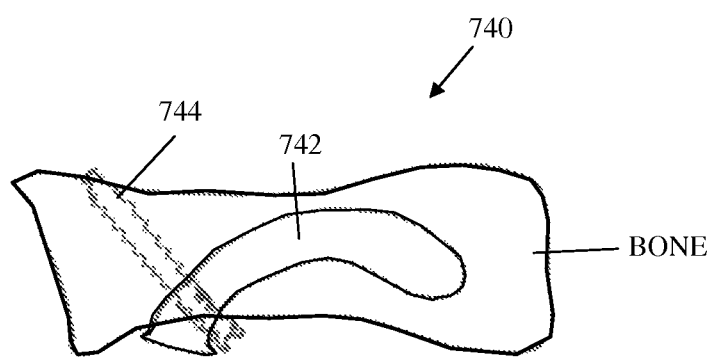
Figure 7E:
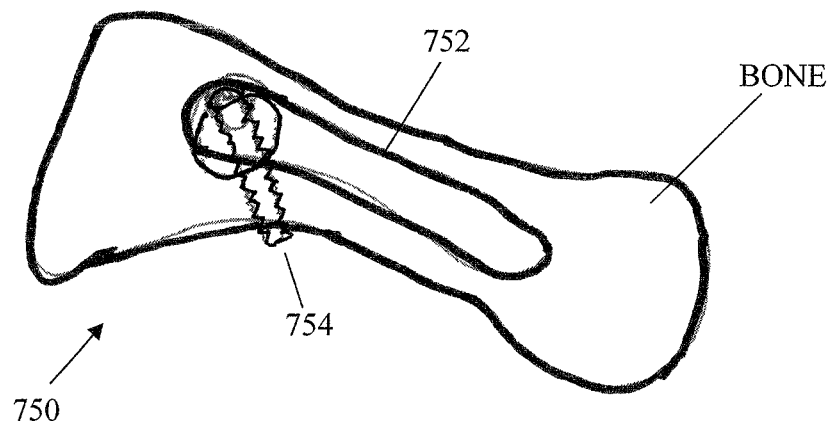

Reference is made now to FIGS. 7A-7E which depict schematic illustrations of arrangements 710, 720, 730, 740 and 750 for fixating intramedullary arm according to embodiments of the present invention. Fixating arrangements 710-750 may be associated with the range of solutions related to the group of fixating means for intramedullary arms that is based on auxiliary fixating means, or interlocking means, mainly interlocking screws. FIG. 7A depicts fixating screw 714 passing through medullar 710, through arm portion 712 and again through medullar 710, providing anti sliding and anti rotational fixation to arm portion 712. FIG. 7B depicts another fixation arrangement where fixating screw 724 may be inserted with arm 722 into the canal of medullar 720 and be tightened by a tool inserted through the entry point to the canal. FIG. 7C depicts the fixated status of the arrangement of FIG. 7B, after fixating screw 724 has been tightened and penetrated from the medullar canal to the bone. FIG. 7D depicts a fixating arrangement where fixating screw 744 is entered through the entry point of arm 742 and than it passes through arm 742 and medullar bone 740 in a direction that is substantially perpendicular to the longitudinal direction of arm 742, thus providing enhanced fixation force.

In the typical form interlocking screws are penetrated from one bone cortex to a usually pre-drilled hole in the device and through it to the cortex on the other side of the bone. For the purpose of stabilizing, the intramedullary arm or rod fixation through one cortex is feasible. This can be by means of a screw that goes from the bone to the fixation device or from the fixation device to the bone. The tunnel within the bone can be with a thread so that the screw is locked in the device. Yet in another embodiment a slot or slots may be made in the intramedullary arm and locked screw may be served to expand the arm's diameter at its passage point through the arm, thus achieving through screwing snug fit of the screw within the intramedullary arm and sung fit of the intramedullary arm within the bone. For such purposes the screw part that affixes within the arm may have a changing diameter.

Figure 8:
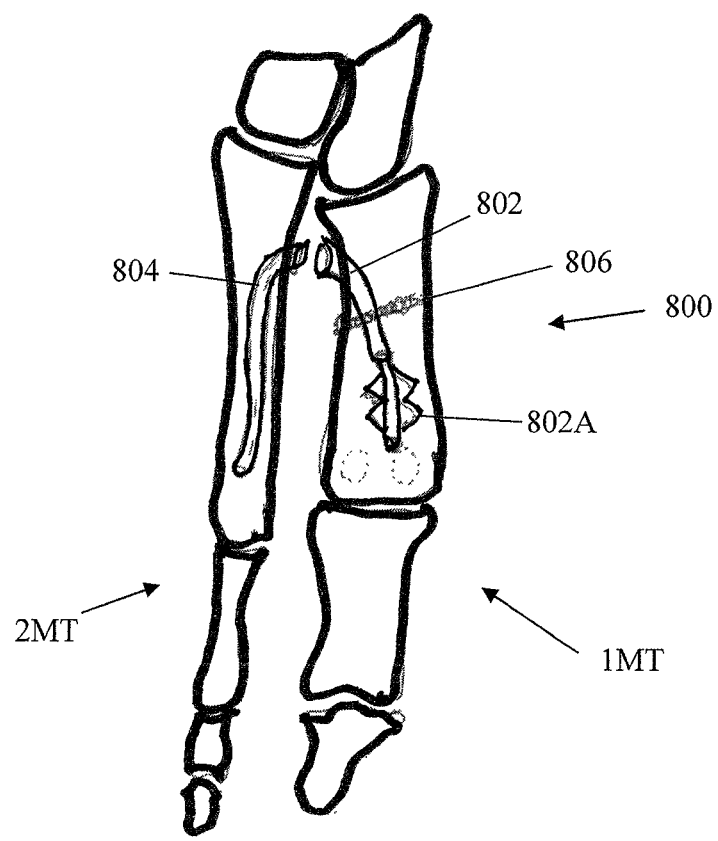
FIG. 8 is a schematic illustration of a HV repair device shown in an partial illustration of bones system of a human foot, according to embodiments of the present invention.

Reference is made now to FIG. 8, which is a schematic illustration of a HV repair device 800 shown in an partial illustration of bones system of a human foot, according to embodiments of the present invention. HV repair device 800 comprising first arm 802 shown inserted into the medullary canal of 1MT, and second arm 804 shown inserted into the medullary canal of 2MT. The spring mechanism was removed for the sake of clarity; however it would be apparent that in a complete HV repair device the spring mechanism is connected between arm 802 and arm 804. Arm 802 is presented equipped with a hybrid fixating mechanism, involving an anchoring arrangement 802A, similar to the device described with regard to FIG. 6C and a fixating screw 806 screwed through the thick second part of 1MT or any other appropriate part of 1MT and through arm 802, thus achieving enhanced fixation force.

Figure 9A:
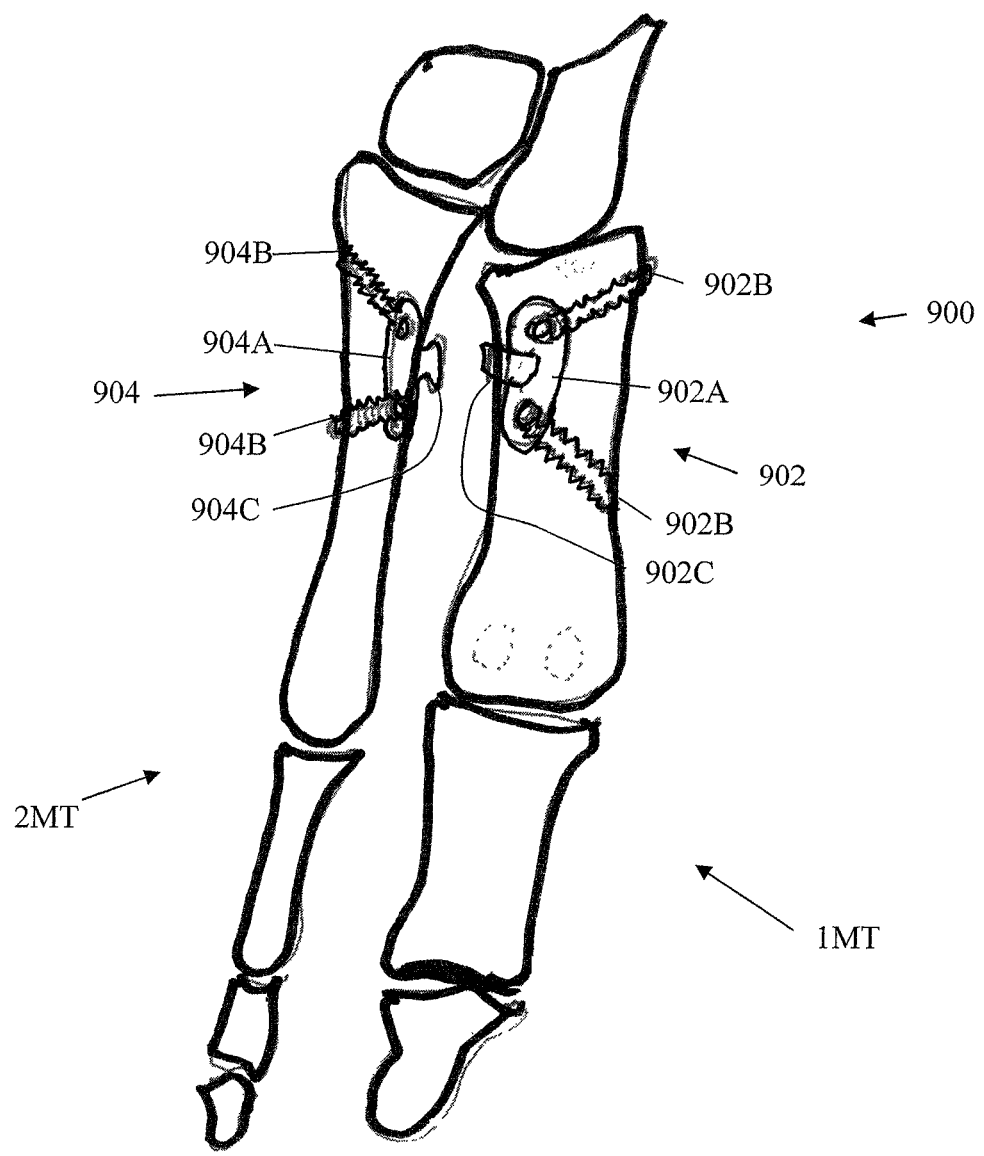
FIGS. 9A and 9B are schematic illustrations of HV repair device using clamp arms and an extended view of one clamp unit, respectively, shown in a partial illustration of bones system of a human foot, according to embodiments of the present invention.
Figure 9B:
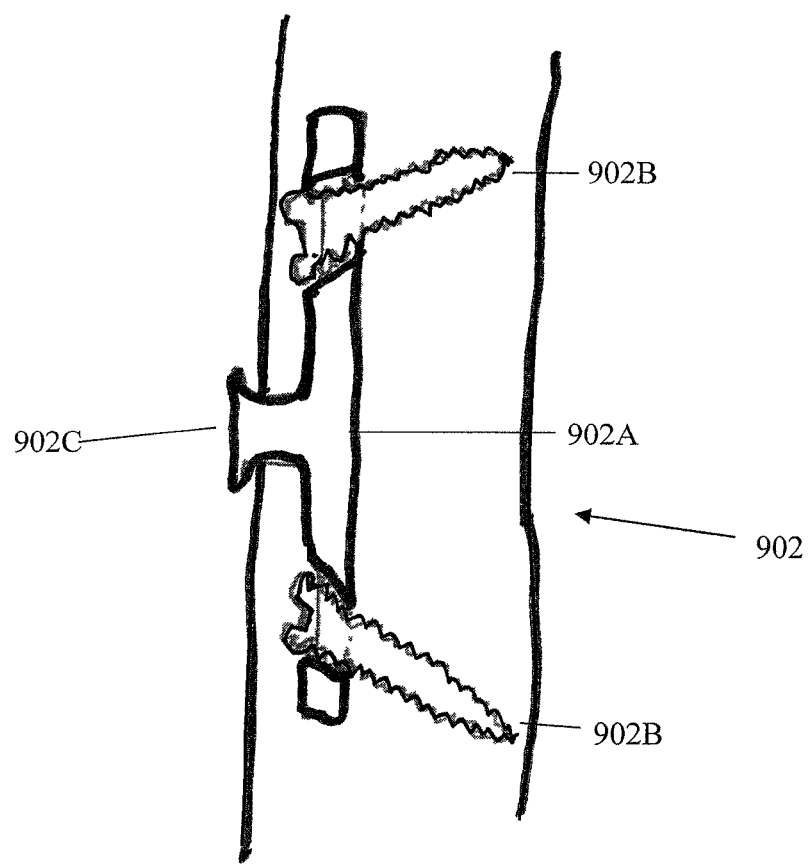

Reference is made now to FIGS. 9A and 9B, which are schematic illustrations of HV repair device 900 using clamp arms and an extended view of one clamp unit 902, respectively, shown in a partial illustration of bones system of a human foot, according to embodiments of the present invention. HV repair device 900 may comprise first clamp arm (locked plate) 902 and second clamp arm (locked plate) 904, each affixed to the outer face of 1MT and 2MT, respectively with locked screws. For enhanced stability and in consideration with the forces that act on the metatarsals the screws may be drilled diagonally in opposing directions. The threaded holes in the locked plate are made to afford it. The spring mechanism was removed for the sake of clarity; however it would be apparent that in a complete HV repair device the spring mechanism is connected between arm 802 and arm 804 via gripping points 902C and 904C, respectively. Arms 902A and 904A may be affixed to the respective MT using 1, 2 or more screws 902B, 904B, as may be required and possible. The fixating solution presented in FIGS. 9A and 9B may be associated with the second group of fixating means for fixating clamping arms including non-embracing arms.

As mentioned above it is crucial that the system will afford relative motion in the vertical plane between the two arms of the device (hence between the two MTs). Since 1MT has motion in the vertical (sagittal) plane in every step and the 2MT has practically no motion (or very little) in the sagittal plane there is relative motion in the sagittal plane between 1MT and 2MT that needs to be enabled. In some constructs no motion is desired between the bone and the device. That sagittal or vertical motion therefore should occur in the spring or the spring mechanism and not transferred to the arms. At the same time the spring should act and induce forces that bring the two arms together. To avoid brakeage of the clip due to a too high rotational strain a spring should afford this type of movement as well. This may be achieved by twisting the spring part so that in one zone it affords axial moments and yet in another zone that is in right angle to the previous one sagittal movement takes place. Reference is made now again to FIG. 2C, in which spring mechanisms 26D and 26E are schematic examples of spring mechanisms which are designed to provide defined lateral (in the plane of the drawing) springy force with much less force exerted in a plane perpendicular to the plane of the drawing.

The motion of the joint between the medial cuneiform and its corresponding 1MT in maneuver moving them upward (dorsiflexion [DF]) and downward (plantar flexion [PF]) is, typically, of 3.5° (range 1.9°-5.3°). The motion between middle cuneiform and its corresponding 2MT is, typically, of 0.6° (range 0.1°-1.0°). There is also a supination movement of the foot, however it was found that in 20° supination motion of the cuneiform, the twist of 1MT joint is 1.3°±1.0°. The average reported motion of the first ray for hallux valgus patients before surgery is 9 mm and the motion is increased with Hyperlaxity and with plantar flexed position of the ankle Since the measurements were done at the proximal part of the metatarsus, e.g. where a device according to embodiments of the present invention is to be inserted, the figures presented above should be considered as the actual movement that the device should accommodate. The spring-like mechanism of a device according to embodiments of the present invention needs to allow almost unrestraint free vertical (sagittal) motion of the 1MT with respect to the 2MT and act in the horizontal plane (the plane of the sole of the foot) to keep the two metatarsal together.

The second MT remains relatively fixed. It is assumed that part of the 1MT motion is rotation around the axis of the 2MT. A device according to embodiments of the present invention needs to afford up to 9-10 mm vertical motion of 1MT in the sagittal plane, while the transverse distance is 15-20 mm after IMA correction. This distance is composed of the width between the cortices, the thickness of the cortices and part of the width of the canal. In between the MT's the distance is more in the order of 10 mm. The spring mechanism should be made accordingly. This may be by selection of configuration and/or materials of the spring, as is known in the art.

The reported motion in midfoot pronation is associated with pronation of the big toe and slight subluxed position of the sesamoids. Since the lateral sesamoid is attached to 2MT through the transverse metatarsal ligament, and is affixed to the 1MT head through the sesamoid metatarsal ligaments, it is considered that in the normal person during gait for a large extent the distance between the distal part of 1MT and 2MT remain relatively constant. The Lisfranc ligament retains a constant distance between the medial cuneiform, which articulates with 1MT and the base of 2MT. According to reasonable approximation, that with the limitation of motion occurring between 1MT and medial cuneiform, and motion between 1MT head and its sesamoid complex, the distance between 1MT and 2MT remains constant. Hence, the documented sagittal motion of the first ray is, to some extent, a radial motion of 1MT on the axis of 2MT.

In cases of severe deformity and very increased IMA, the pressure that the spring applies on the MT's might be too high with risk of stress fracture. To reduce the initial pressure the spring mechanism may be designed to have springy effect that maintains pulling force at substantially same amount regardless of the value of IMA, or limits the springy force under a defined limitation at high values of IMA as is known in the art. Similarly, the spring mechanism may be adjustable, so to allow the adjustment of force as needed, both during the surgical operation and/or afterwards.

Bunionette deformity and affiliated conditions often are composed of valgus deviation of the 5$^{th}$ metatarsal (5MT), away from the 4$^{th}$ MT (4MT) thus creating a large intermetatarsal angle between them (4-5 IMA). The common consequences or accompaniments of wide 4-5 IMA is the creation of painful bony prominence on the lateral aspect of the foot, at the level of the 5MT head. This is similar to and in some respects a mirror image of the same deformity involving the big toe, the bunion. Since this involves the lesser toe complex it is called bunionette. In bunionette deformity the 5$^{th}$ toe often drift into varus. Splay foot is a situation, in which the foot is wide and often causes difficulty in foot wear. This situation usually is composed mainly of increased 1-2 IMA as well as 4-5 IMA. Often the prior art correction of this malady entails osteotomy of the 5MT and shifting its head medially, thus narrowing the 4-5 IMA. The arms and spring mechanism which were described above with respect to the repair of 1MT-2MT HV are applicable to the 4MT-5MT extended IMA, with the required changes, mainly due to smaller dimensions of the cortex and its canals.

Figure 10:
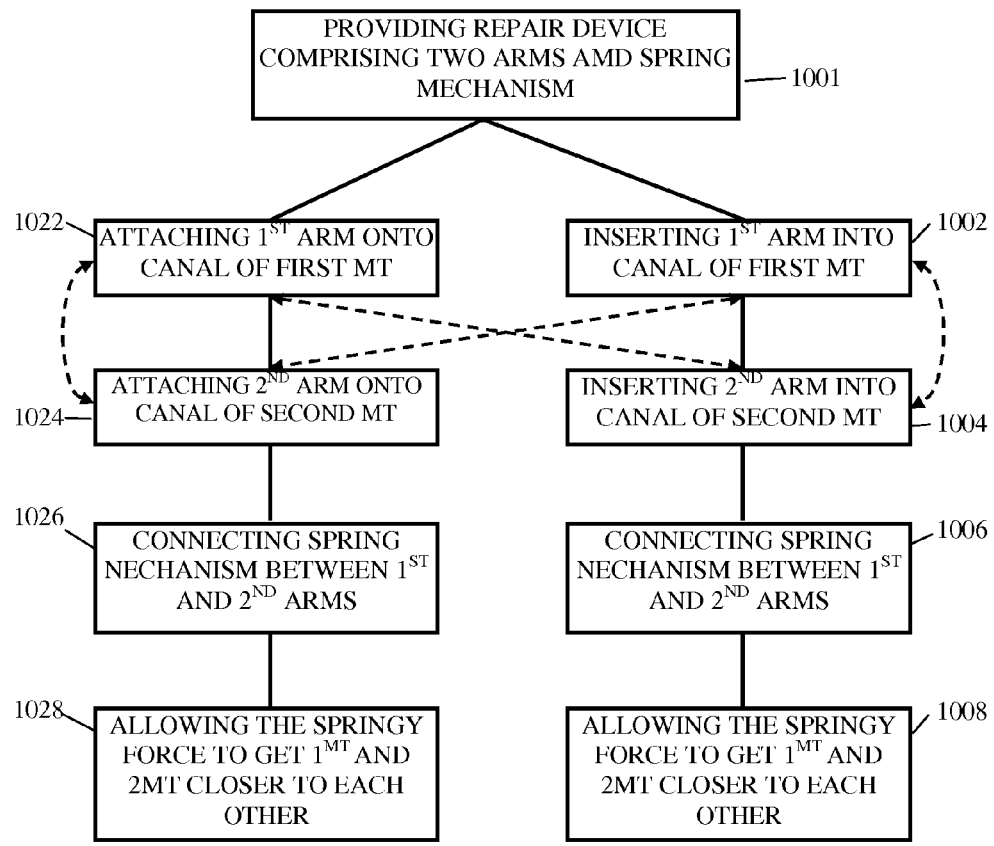
FIG. 10 is a flow chart depicting methods for repairing Hallux valgus according to embodiments of the present invention.

Reference is made to FIG. 10, which is a flow chart depicting methods for repairing Hallux valgus according to embodiments of the present invention. A repair device according to embodiments of the present invention, comprising two arms and a spring mechanism, is provided (block 1001). If the method of installation is intramedullary the first arm is inserted into a medullary canal of 1 MT and affixed there (block 1002) and second arm is inserted into the intramedullary canal of 2MT and affixed (block 1004). Spring mechanism is connected between gripping points on the first and the second arms (block 1006) and the influence of the torque produced between 1MT and 2MT is allowed to take effect (block 1008). It will be appreciated by those skilled in the art that different order of application of the actions associated with blocks 1002, 1004, 1022 and 1024. Accordingly the order may change to be 1004 then 1002, or 1002 and then 1024, or 1004 and then 1022, etc., any order that attaches an arm to 1MT and to 2MT, as may be found desirable by the physician or surgeon.

Similarly when the method of installation is selected by affixing the arms onto the outer face of the respective MT, after performing the operations of block 1001 the first arm is attached to the outer face o1 MT and affixed to it (block 1022), the second arm is attached to the outer face of 2MT and affixed to it (block 1024) and a spring mechanism is connected between gripping points of the first and the second arms (Block 1026). Finally, and the influence of the torque produced between 1MT and 2MT is allowed to take effect (block 10208).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A device for repairing Hallux Valgus (HV) comprising:
   a. a first arm adapted to be longitudinally disposed in the first metatarsus (1MT) of a human foot;
   b. a second arm adapted to be longitudinally disposed in the second metatarsus (2MT) of a human foot; and
   c. a spring mechanism interconnecting said first arm and said second arm, operable to draw said 1MT and 2MT together;
   wherein at least one of said arms further comprises fixing means adapted for fixation of said first and/or second arm inside the canal of the respective first and/or second metatarsus; and
   wherein said spring mechanism comprises first and second extending portions that provide a first spring force between said first and said second arms about a pivot point in a first plane being the plane common to said 1MT and 2MT and a second spring force, less than the first spring force, between said 1MT and 2MT in a second plane not coincident with said first plane.

2. The device of claim 1, wherein said spring mechanism is releasably connectable to said first and second arms.

3. The device of claim 2, wherein said spring mechanism is adapted to be connected to said first and second arm after installing and affixing said first and second arm within said 1MT and 2MT respectively.

4. A device for repairing Hallux Valgus (HV) comprising:
   a. a first arm adapted to be longitudinally disposed in the first metatarsus (1MT) of a human foot;
   b. a second arm adapted to be longitudinally disposed in the second metatarsus (2MT) of a human foot; and
   c. a spring mechanism interconnecting said first arm and said second arm, operable to draw said 1MT and 2MT together;
   wherein at least one of said first and second arms is shaped in a longitudinal tubular arc-like manner for fixation of said first and/or second arm inside the canal of the respective first and/or second metatarsus; said arm is provided with a gripping point connecting said spring mechanism thereto.

5. A device for repairing Hallux Valgus (HV) comprising: a first arm adapted to be affixed inside the canal of the first metatarsus (1MT) of a human foot; a second arm adapted to be affixed inside the canal of the second metatarsus (2MT) of a human foot; and a spring mechanism interconnecting said first arm and said second arm, adapted to draw said first and second arms together; wherein
   at least one of said arms comprises a curved elongated member adapted to be longitudinally disposed in and fitted snugly in zone 3 of a medullary canal of 1MT or 2 MT and having a curved and tapered tip for insertion longitudinally in the medullary canal; and wherein
   the spring mechanism comprises first and second spring attachments, each adapted to be attached at a respective attachment end thereof to the respective first and second arms, and a spring between the first and second spring attachments and opposite the attachments ends of the first and second arms.

* * * * *